(12) United States Patent
Behr et al.

(10) Patent No.: US 8,802,640 B2
(45) Date of Patent: Aug. 12, 2014

(54) OLIGONUCLEOTIDES FOR RNA INTERFERENCE AND BIOLOGICAL APPLICATIONS THEREOF

(75) Inventors: Jean-Paul Behr, Strasbourg (FR); Anne-Laure Bolcato Bellemin, Strasbourg (FR); Patrick Erbacher, Benfeld (FR)

(73) Assignee: Polyplus-Transfection SA, Illkirch (FR)

( * ) Notice: Subject to any disclaimer, the term of this patent is extended or adjusted under 35 U.S.C. 154(b) by 411 days.

(21) Appl. No.: 11/921,089

(22) PCT Filed: Jun. 1, 2006

(86) PCT No.: PCT/EP2006/006340
§ 371 (c)(1),
(2), (4) Date: Jan. 30, 2008

(87) PCT Pub. No.: WO2006/128739
PCT Pub. Date: Dec. 7, 2006

(65) Prior Publication Data
US 2008/0153772 A1    Jun. 26, 2008

Related U.S. Application Data

(60) Provisional application No. 60/686,010, filed on Jun. 1, 2005.

(51) Int. Cl.
*C07H 21/00* (2006.01)

(52) U.S. Cl.
USPC .................. 514/44 A; 536/24.5; 435/91.1

(58) Field of Classification Search
CPC .................................................. C12N 2310/51
See application file for complete search history.

(56) References Cited

U.S. PATENT DOCUMENTS

| | | | |
|---|---|---|---|
| 6,506,559 B1 * | 1/2003 | Fire et al. | 435/6 |
| 8,362,231 B2 | 1/2013 | Tuschl et al. | |
| 2003/0143732 A1 * | 7/2003 | Fosnaugh et al. | 435/325 |
| 2003/0148507 A1 * | 8/2003 | Fosnaugh et al. | 435/320.1 |
| 2003/0212022 A1 * | 11/2003 | Vogel et al. | 514/44 |

OTHER PUBLICATIONS

Definition of Oligomer from the Oxford Dictionary of Biochemistry and Molecular Biology, Revised Edition, Oxford University Press.*
International Search Report mailed Nov. 2, 2006.
Elbashir S.M. et al.: "RNA interference is mediated by 21- and 22-nucleotide RNAs," Genes and Development, Cold Spring Harbor Laboratory Press, Plainview, NY, US, vol. 15, No. 2, Jan. 15, 2001, pp. 188-200, XP002204651.
Elbashir S.M. et al.: "Functional anatomy of siRNAs for mediating efficient RNAi in *Drosophila melanogaster* embryo lysate," Embo Journal, Oxford University Press, Surrey, GB, vol. 20, No. 23, Dec. 3, 2001, pp. 6877-6888, XP002225998.
Vermeulen A. et al.: "The contributions of dsRNA structure to Dicer specificity and efficiency," RNA, vol. 11, Apr. 5, 2005, pp. 674-682, XP002403258.
Declaration of Patrick Erbacher executed May 16, 2013 (22 pages).
"Table 1" from "Negotiating the RNAi Patent Thicket" (Schmidt, Nature Biotechnology 25, 273-275 (2007)).
"RNAi Litigation" Thomas Tuschl's Inventive Work on Tuschl II in His Own Words. Jul. 10, 2012 printed Mar. 21, 2013 from http:/blog.nerac.com/rnailitigation/2012/07/10.
Sen et al "A brief history of RNAi: the silence of genes," The FASEB Journal 20, 1293-1299 (Jul. 2006).
Chang et al ("Structural Diversity Repertoire of Gene Silencing Small Interfering RNAs" Nucleic Acid Therapeutics, vol. 21, No. 3 (2011), pp. 125-131.
Sarkar et al, "Condensation of oligonucleotides assembled into nicked and gapped duplexes: potential structures for oligonucleotide delivery", Nucleic Acids Research, 2005, vol. 33, No. 1, 143-151.

* cited by examiner

*Primary Examiner* — Jennifer McDonald
(74) *Attorney, Agent, or Firm* — Nixon & Vanderhye P.C.

(57) ABSTRACT

The invention relates to compositions comprising double-stranded oligonucleotides of identical or different sequences and/or length, said oligonucleotides having sequences $^{3'}N_1 N_2 \ldots N_{i-1} N_i \ldots N_j^{5'}$ wherein—$^{3'}N_i \ldots N_j^{5'}$ is half of a double-stranded 19-28mer oligonucleotide of sequence complementary to a target nucleic acid sequence present in a living cell, and—$^{3'}N_1 \ldots N_{i-1}^{5'}$ is a 3-50mer overhang of sequence allowing oligomerization of said double-stranded oligonucleotide. Compositions of transfection comprising said oligonucleotide compositions and there used for therapeutical application.

11 Claims, 10 Drawing Sheets

OLIGONUCLEOTIDES FOR RNA INTERFERENCE AND BIOLOGICAL APPLICATIONS THEREOF

Figure 1A:
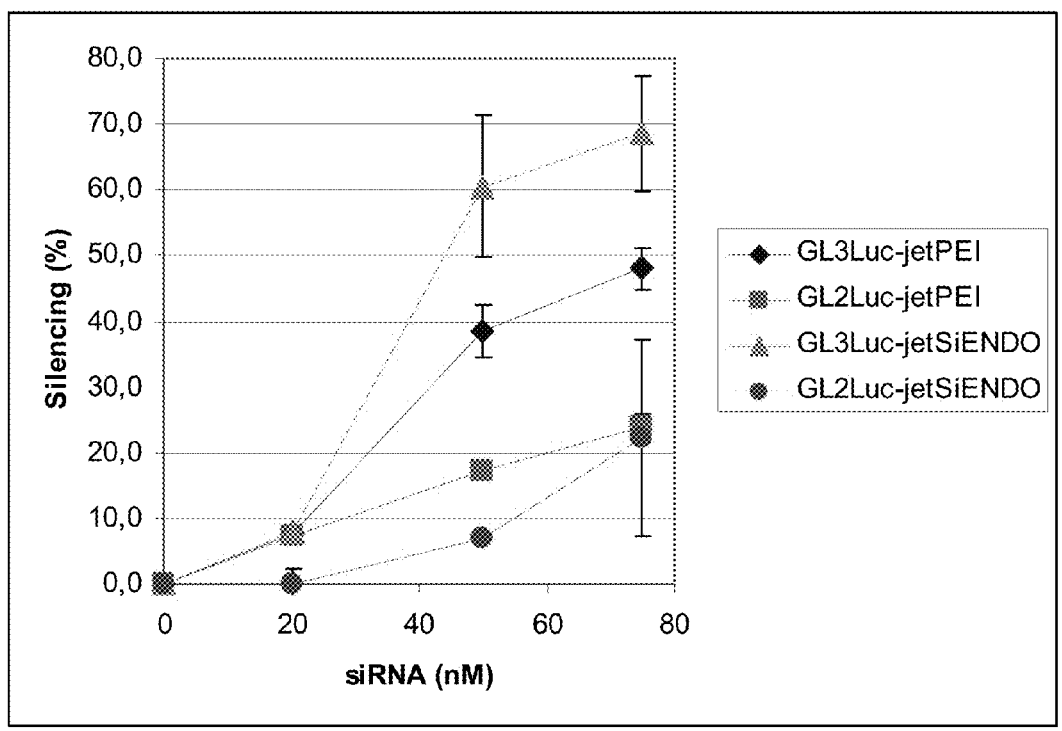

This application is the US national phase of international application PCT/EP2006/006340 filed 1 Jun. 2006, which designated the U.S. and claims benefit of U.S. Provisional No. 60/686,010, filed 1 Jun. 2005, the entire contents of each of which are hereby incorporated herein by reference.

The invention relates to new double stranded oligonucleotides (dsONs) useful for RNA interference. It also relates to their use for oligonucleotides delivery to eukaryotic cells in culture or in animals for biological or therapeutic uses.

RNA interference (RNAi) is now a technology for gene silencing at the early gene function level, the mRNA (Fire et al, 1999; Tuschl et al., 1999). The technology provides sequence-specific mRNA degradation and inhibition of protein production (Yang et al, 2000, Zamore et al, 2000, Hammond et 2000, Parrish 2000). RNAi is highly effective due to a predictable design of active sequences of short dsRNA (siRNA, for small interfering RNA) and to the targeting of mRNA. When siRNA duplexes are introduced by transfection with a vector and delivered into the cytoplasm, RNAi has been shown to effectively silence exogenous and endogenous genes in a variety of mammalian cells (Elbashir et al, 2001).

Structural features of conventional dsRNA molecules required to mediate RNAi demonstrate that short dsRNAs having a length of preferably from 19-25 nucleotides (see patents WO 0244321, WO 01/075164 A3, EP20010985833), particularly 19-23 nucleotides, have RNAi activity in mammalian cell culture systems (Parrish et al., 2000; Elbashir et al., 2001; Tuschl, 2001). Short 19-25 nucleotides, when base-paired, with unpaired 3' overhanging ends, act as the guide for sequence-specific mRNA degradation. It is possible to observe RNAi when both ends are blunt (0 nucleotide overhang) or when one strand is blunt-ended. Even if the sequence of the unpaired overhang of the siRNA is not critical for target RNA cleavage, the presence of 3' overhang appears critical for optimized RNAi and stability of siRNA. Preferably, at least one strand has a 3'-overhang from 1 to 5 nucleotides, particularly from 1 to 3 nucleotides. The RNA strands preferably have 3'-hydroxyl groups and preferably comprise phosphate groups at the 5'-terminus, without 5'-overhangs. The most effective short dsRNAs are composed of two 21 nucleotides strands which are paired such that 1-3, particularly 2, nucleotides 3'-overhangs are present on the both ends of the dsRNA (Elbashir et al., 2001). The length of the RNA duplex was shown to be extendable to 27-28mer (Siolas et al., 2005, Kim et al., 2005) and to tolerate various chemical and or backbone modifications (Kurreck, 2003).

The success of RNAi depends both on dsRNA length, sequence and chemical structure and on vector for cellular delivery. As compared to antisense or ribozyme technology, the secondary structure of the target mRNA is not a strong limiting factor for silencing with siRNA. Many sequences of siRNA may be effective for a given mRNA target. Thus, the stability and bioavailability of siRNA duplexes as well as the amount of dsRNA delivered to cells remains the limiting factors for efficient silencing rather than the target accessibility by the siRNA.

The inventors have found that dsONs with particular structural features that allow them to stick to each others have a high RNA interference activity in eukaryotic cells and provide higher gene silencing efficiencies than those obtained using conventional short dsRNAs, when introduced with as the same delivery system. Longer oligonucleotides than conventional short dsRNA exhibit a higher stability due to their better resistance to degradation.

It is then an object of the invention to provide new compositions comprising dsONs that are sequence-specific mediators of RNAi when introduced in mammalian cells. The invention thus describes the benefit for gene silencing of dsONs containing many copies of short dsONs mediating sequence-specific RNA interference of one or many targeted genes.

It also relates to various transfection delivery systems based on synthetic carriers and their use in biological applications.

The compositions of the invention comprise double-stranded oligonucleotides of identical or different sequences or length, said oligonucleotides having sequences $^{3'}N_1N_2 \ldots N_{i-1}N_i \ldots N_j^{5'}$ wherein $^{3'}N_i \ldots N_j^{5'}$ is half of a double-stranded 19-28mer oligonucleotide of sequence complementary to a target nucleic acid sequence present in a living cell, and $^{3'}N_1 \ldots N_{i-1}^{5'}$ is a 3-50mer overhang of sequence allowing oligomerisation of said double-stranded oligonucleotide.

Preferred dsONs of said compositions advantageously have a sequence $^{3'}N_i \ldots N_j^{5'}$ of 19-21 nucleotides and/or a sequence $^{3'}N_1 \ldots N_{i-1}^{5'}$ comprising 5 to 8 nucleotides.

As demonstrated in the examples, short dsONs, when base-paired with unpaired 3' overhanging ends, and oligomerized in long dsON, act as guides for sequence-specific mRNA degradation.

According to an embodiment of the invention, sequences $^{3'}N_1 \ldots N_{i-1}^{5'}$ may be stabilized against degradation, for example by nucleases, without significant loss of activity. Suitable stabilizing groups are selected in the group comprising purine nucleotides, pyrimidine nucleotides substituted by modified analogs such as deoxynucleotides, and/or modified nucleotide analogs such as sugar- or backbone modified ribonucleotides or deoxyribonucleotides.

In another embodiment, optionally in combination with anyone of the preceding features, the compositions of the invention comprise at least one dsON with a 5' phosphate or hydroxyl group at one or both 5' ends.

In the dsONs of the compositions according to the invention, the oligonucleotides sequences contain deoxyribonucleotides, ribonucleotides or nucleotide analogs (Verma and Eckstein, 1998), such as methylphosphonate (Miller, 1991), morpholino phosphorodiamidate, phosphorothioate (Zon and Geiser, 1991), PNA (Jepson and Wengel, 2004), LNA, 2' alkyl nucleotide analogs (Kurreck, 2003).

Potent viral or non-viral vectors are useful for introducing oligonucleotides in cells. Viral delivery systems still suffer from their immunogenicity and potential risk in clinical situations. In contrast, the transfection of nucleic acids with synthetic systems is a versatile method showing flexibility and absence of immunogenicity. The transfection of oligonucleotides with non-viral vectors is useful for the delivery of dsONs in the cytoplasm. Currently non-viral vectors are mainly based on cationic lipids-mediated transfection, such as Oligofectamin, TRANSIT-TKO, LipofectAmine-2000, SiGuide, RNAiFect, or jetSi, or based on cationic polymer-mediated transfection, such as Superfect, jetPEI, or X-TREMGene.

The invention thus also relates to transfection compositions comprising at least an oligonucleotide composition such as above defined and a transfection agent or formulation.

The transfection agent or formulation is more particularly a non-viral delivery system suitable for introducing dsONs in living cells and liberating dsONs mediating RNAi in cells.

The non viral vector system advantageously comprises cationic lipid- or polymer- or peptide-based delivery reagents. The non-viral vector system is a formulation comprising at least a delivery reagent and others components stabilizing the formulation, targeting the cells, tissues or organs, or increasing the transfection efficiency.

When complexed with transfection reagents prior to introduction into the cells, the oligomerization of short dsONs is promoted by intermolecular interactions due to a 3'-overhang-3'-overhang interaction or by using a linker that interacts with 3' overhangs of dsONs. Many linkers can be used such as oligonucleotides that comprise sequences of nucleotides complementary to the 3'-overhangs of dsONs that mediate RNAi. Others linkers can be: i) hairpin-like structure having terminal oligomerization domains that recognize the 3' overhangs of dsONs mediating the RNAi, ii) short double stranded nucleic acid having 5'- or 3'-overhangs at each strand end which recognize the 3'-overhangs of dsONs mediating RNAi. The linker can also be one or several dsON (or many dsONs) that mediate sequence-specific RNAi or not and comprising overhangs that interact with 3'-overhangs of dsON mediating gene silencing by RNAi.

The invention also relates to a process for preparing a composition of oligonucleotides such as above defined, said process comprising synthetizing oligonucleotide strands having sequences $_{3'}N_i \ldots N_j{}^{5'}$ and $^{3'}N_1 \ldots N_{i-1}{}^{5'}$ such as above defined by a chemical or enzymatic way;

annealing the synthetized oligonucleotides thus obtained

According to an embodiment, said process further comprises adding linker(s) after the annealing step of said oligonucleotides, said linker(s) having nucleotidic sequences ends complementary to sequence $^{3'}N_1 \ldots N_{i-1}{}^{5'}$.

Said linker(s) is (are) advantageously selected in the group comprising oligonucleotides, single-stranded oligonucleotides, hairpin-like structures, short double-stranded nucleic acids having 3' or 5' overhangs, double stranded oligonucleotides.

The linkers are selected in the group comprising deoxyribonucleotides, ribonucleotides or nucleotide analogs.

The invention also relates to a method for in vitro and in vivo inhibition of gene expression, comprising the use of an oligonucleotide composition or a transfection composition such as above defined.

Said compositions and method are particular useful for therapeutical applications such as treatment of cancers, such as bladder (Urban-Klein et al., 2004), prostate (Pal et al., 2005) or leukaemia (Guan et al., 2005) cancers, or viral infections, such as HIV, Hepatitis virus, or influenza virus infections (Ge et al., 2004).

Other characteristics and advantages of the invention will be given in the following, with reference to FIGS. 1 to 7, which represent, respectively:

BRIEF DESCRIPTIONS OF THE FIGURES

FIG. 1A: Luciferase gene expression of A549-GL3Luc cells, as described herein, measured after 24 h. Experiments are made in triplicate and the GL3 luciferase silencing efficiency was calculated from the endogenous luciferase level of nontransfected A549-GL3Luc cells normalized by the content of protein in cell lysates.

Figure 1B:
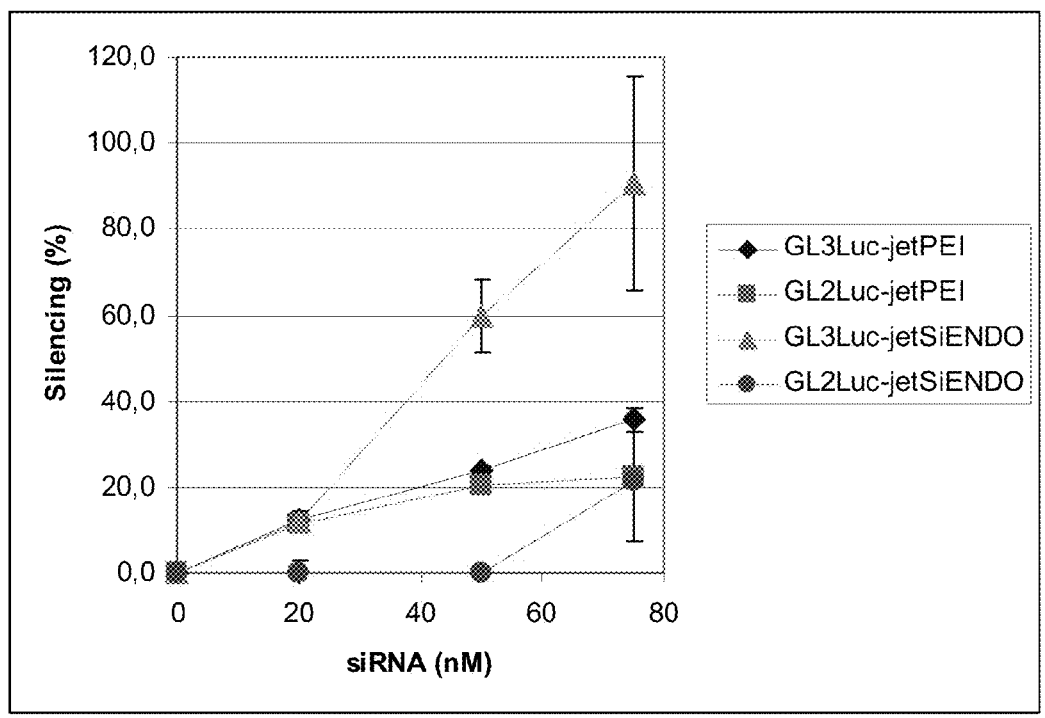

FIG. 1B: Luciferase gene expression of A549-GL3Luc cells, as described herein, measured after 48 h. Experiments are made in triplicate and the GL3 luciferase silencing efficiency was calculated from the endogenous luciferase level of nontransfected A549-GL3Luc cells normalized by the content of protein in cell lysates.

Figure 2A:
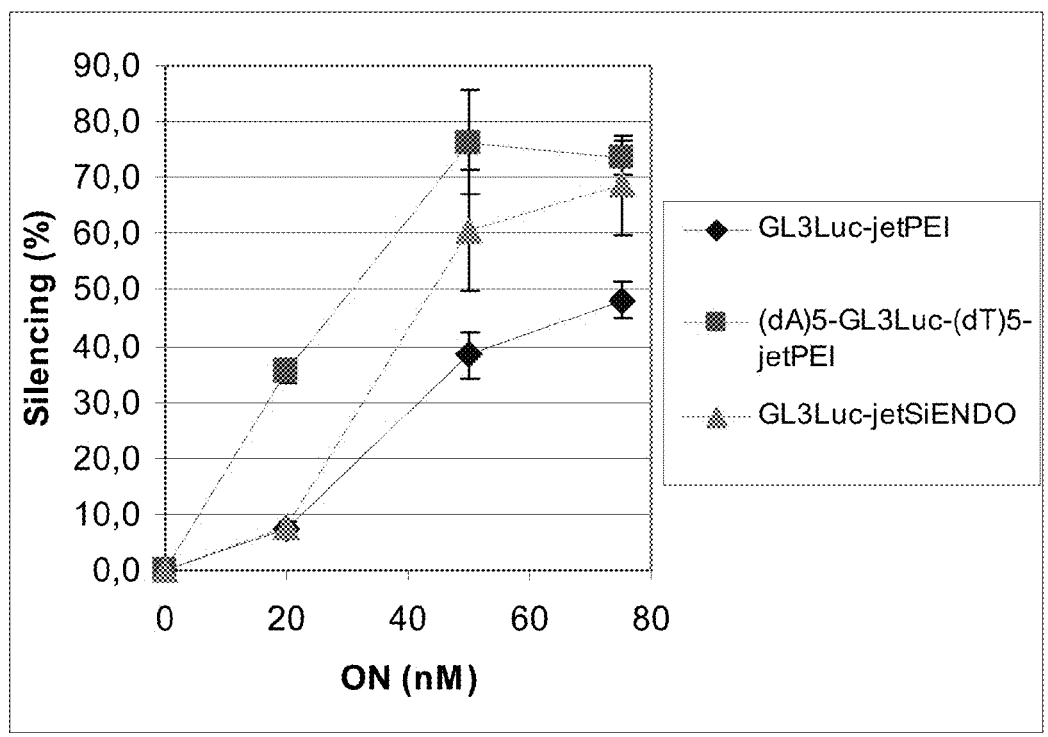

FIG. 2A: Luciferase gene expression of A549-GL3Luc cells, as described herein, measured after 24 h. Experiments are made in triplicate and the GL3 luciferase silencing efficiency was calculated from the endogenous luciferase level of nontransfected A549-GL3Luc cells normalized by the content of protein in cell lysates.

Figure 2B:
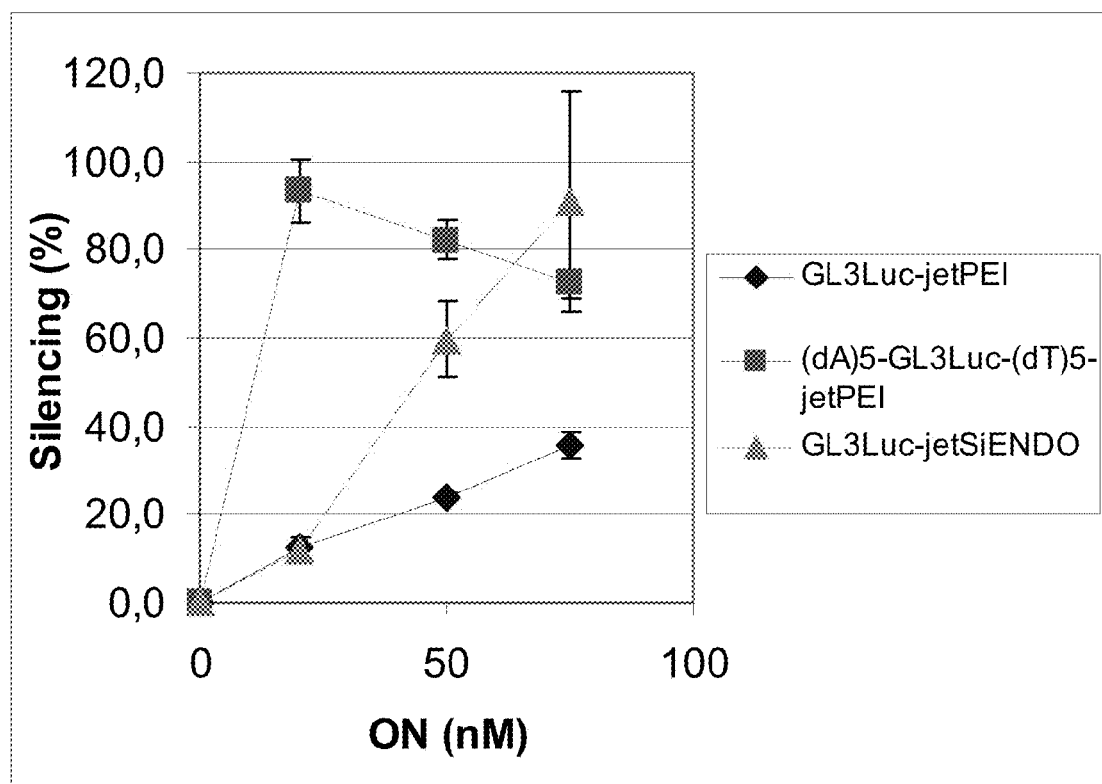

FIG. 2B: Luciferase gene expression of A549-GL3Luc cells, as described herein, measured after 48 h. Experiments are made in triplicate and the GL3 luciferase silencing efficiency was calculated from the endogenous luciferase level of nontransfected A549-GL3Luc cells normalized by the content of protein in cell lysates.

Figure 3:
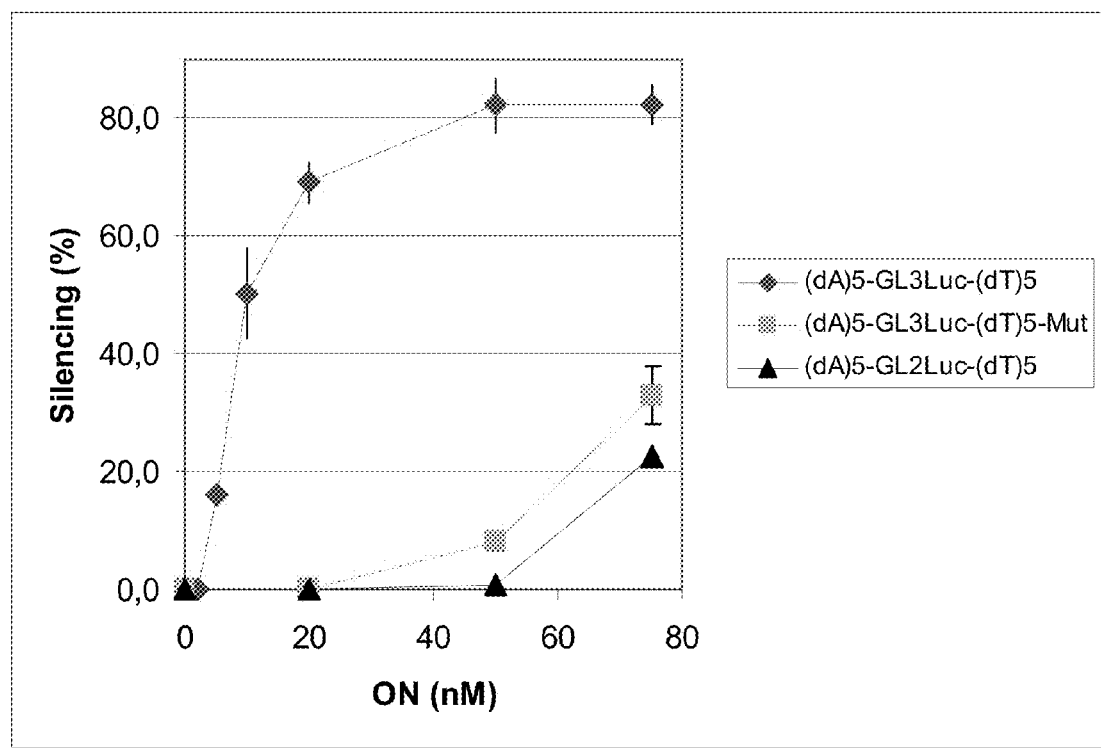

FIG. 3: RNA interference by (dA)5-GL3Luc-(dT)5 d5RNA (SEQ ID NOs: 5 and 6) duplexes mediates sequence-specific RNA interference. Experiments are made in triplicate and the GL3 luciferase silencing efficiency was calculated from the endogenous luciferase level of nontransfected A549-GL3Luc cells normalized by the content of protein in cell lysates.

Figure 4:
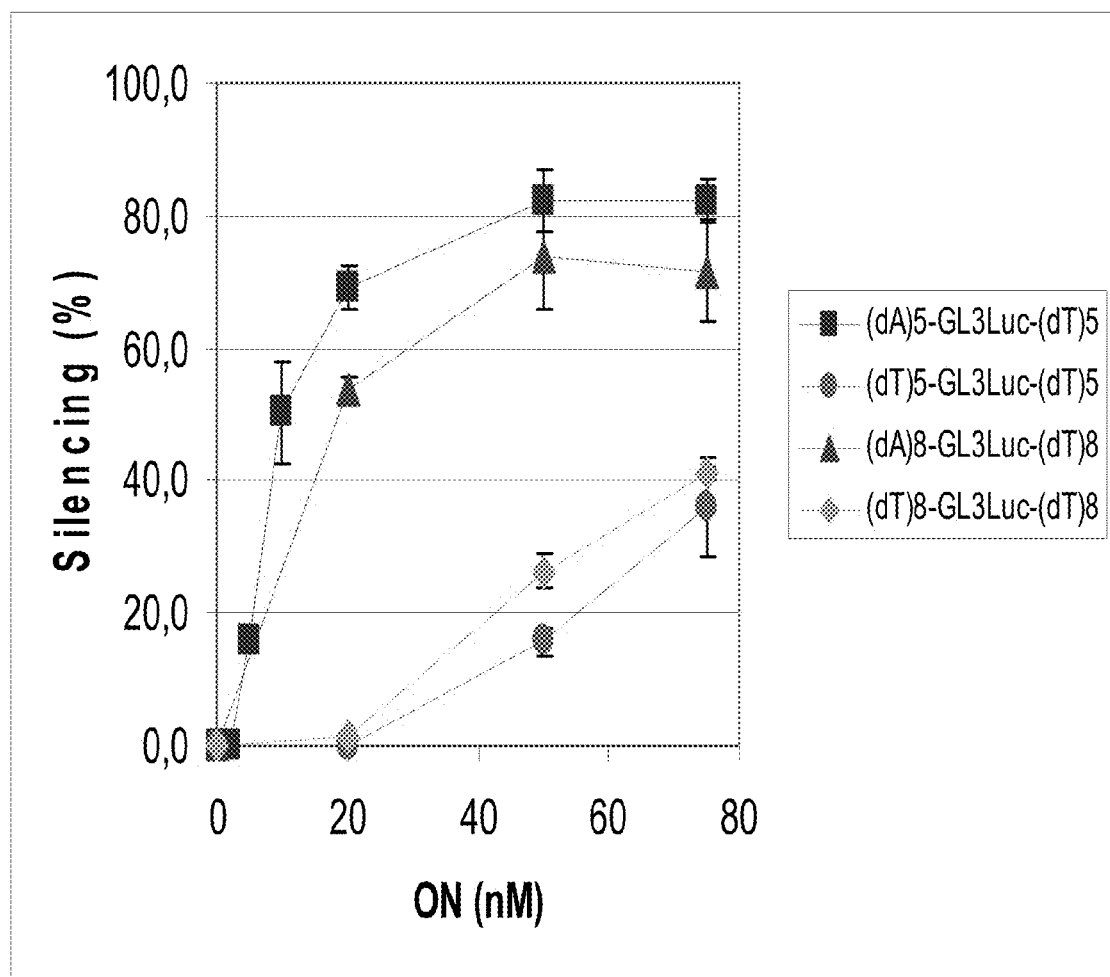

FIG. 4: Double-stranded RNA having 3'-overhang that induce their intermolecular oligomerization when complexed with jetPEI™ mediates high GL3Luciferase silencing. Experiments are made in triplicate and the GL3 luciferase silencing efficiency was calculated from the endogenous luciferase level of nontransfected A549-GL3Luc cells normalized by the content of protein in cell lysates.

Figure 5:
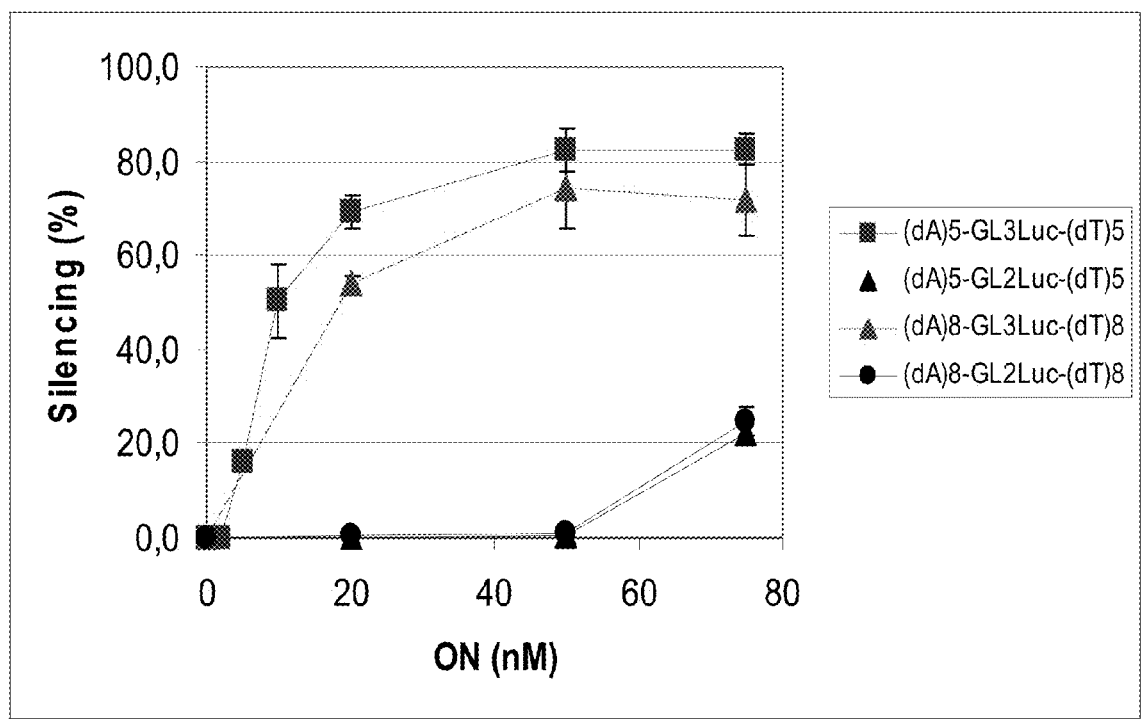

FIG. 5: Double-stranded RNA having 3'-overhang that induce their intermolecular oligomerization when complexed with jetPEI™ mediates a sequence-specific GL3Luciferase silencing. Experiments are made in triplicate and the GL3 luciferase silencing efficiency was calculated from the endogenous luciferase level of nontransfected A549-GL3Luc cells normalized by the content of protein in cell lysates.

Figure 6:
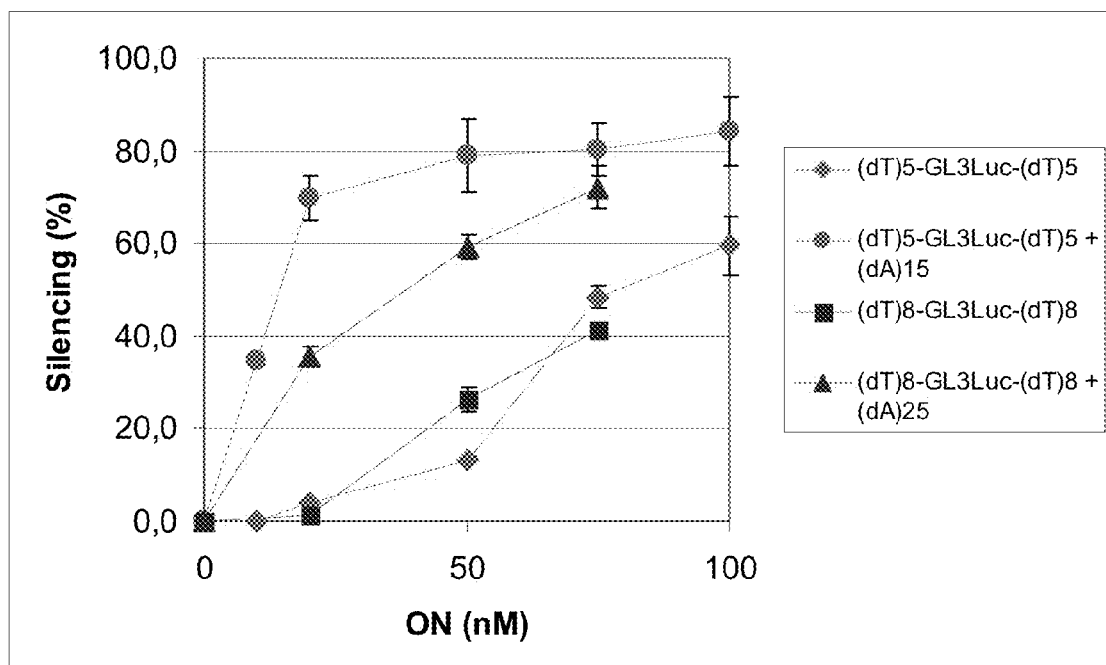

FIG. 6: Oligomerization of d5RNA promoted by intermolecular interactions using a linker interacting with symmetric 3'overhangs of dsRNAs duplexes mediates efficient GL3Luciferase silencing when complexed with jetPEI™. Experiments are made in triplicate and the GL3 luciferase silencing efficiency was calculated from the endogenous luciferase level of nontransfected A549-GL3Luc cells normalized by the content of protein in cell lysates.

Figure 7A:
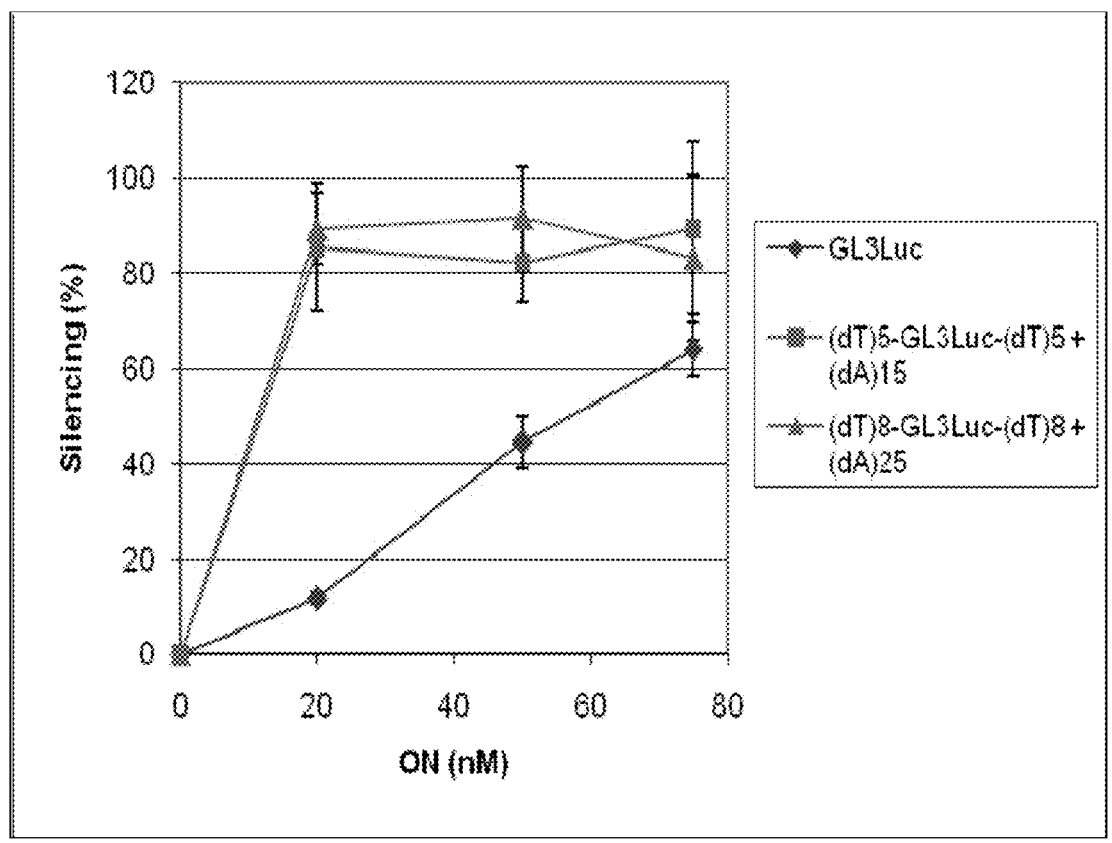

FIG. 7A: Oligomerization of dsRNA promoted by intermolecular interactions using a linker interacting with symmetric 3'overhangs of dsRNAs duplexes mediates efficient GL3Luciferase silencing when complexed with a cationic lipid formulations such as jetSi-ENDO™. Experiments are made in triplicate and the GL3 luciferase silencing efficiency was calculated from the endogenous luciferase level of nontransfected A549-GL3Luc cells normalized by the content of protein in cell lysates.

Figure 7B:
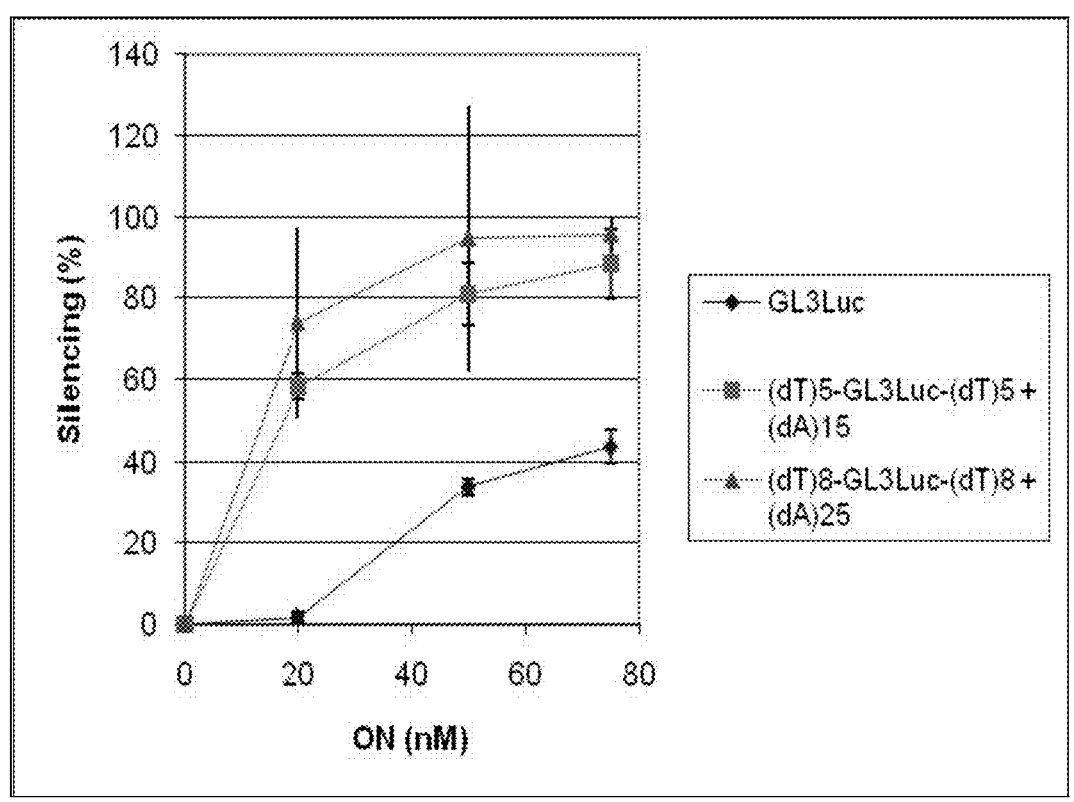

FIG. 7B: Oligomerization of dsRNA promoted by intermolecular interactions using a linker interacting with symmetric 3'overhangs of dsRNAs duplexes mediates efficient GL3Luciferase silencing when complexed with a cationic lipid formulations such as RNAiFect. Experiments are made in triplicate and the GL3 luciferase silencing efficiency was calculated from the endogenous luciferase level of nontransfected A549-GL3Luc cells normalized by the content of protein in cell lysates.

FIG. 1: RNA interference by conventional siRNA duplexes complexed with representatives of the two major classes of transfection reagents, i.e., a cationic lipid-based and a polymer-based transfection reagent (jetSi-ENDO™ and jetPEI™, respectively).

A549-GL3Luc cells, stably expressing the GL3 luciferase gene, were transfected with GL3Luc siRNA complexed with jetSi-ENDO™ and jetPEI™ to evaluate the potency of transfection reagents. Luciferase gene expression was measured after 24 h (a) and 48 h (b) incubation period. Cell lysates were assessed for firefly luciferase expression using a commercial kit (Promega). As nonspecific control, siRNA matching the GL2 luciferase sequence are transfected in the same conditions. Experiments are made in triplicate and the GL3 luciferase silencing efficiency was calculated from the endogenous luciferase level of nontransfected A549-GL3Luc cells normalized by the content of protein in cell lysates.

GL3Luc siRNA (SEQ ID NO:1/SEQ ID NO:2): SEQ ID NO:1: 5'-CUUACGCUGAGUACUUCGA(dT)$_2$-3'; SEQ ID NO: 2: 3'-(dT)$_2$GAAUGCGACUCAUGAAGCU-5'; GL2Luc siRNA (SEQ ID NO:°3/SEQ ID NO:4): SEQ ID NO:3: 5'-CGUACGCGGAAUACUUCGA(dT)$_2$-3'; SEQ ID NO:4: 3'-(dT)$_2$GCAUGCGCCUUAUGAAGCU-5'.

FIG. 2: RNA interference by (dA)$_5$-GL3Luc-(dT)$_5$ dsRNA (SEQ ID NOs: 5 and 6) duplexes complexed with a cationic polymer delivery reagent, jetPEI™.

A549-GL3Luc cells were transfected and luciferase gene expression was measured after 24 h (a) and 48 h (b) incubation period. Standard GL3Luc siRNA (SEQ ID NOs: 1 and 2) was used for comparison. Experiments were made in triplicates and the luciferase silencing efficiency was calculated from the endogenous luciferase level of nontransfected A549-GL3Luc cells normalized by the content of protein in cell lysates.

GL3Luc siRNA (SEQ ID NO:1/SEQ ID NO:2): SEQ ID NO:1: 5'-CUUACGCUGAGUACUUCGA(dT)$_2$-3'; SEQ ID NO:2: 3'-(dT)$_2$GAAUGCGACUCAUGAAGCU-5'; (dA)$_5$-GL3Luc-(dT)$_5$ dsRNA (SEQ ID NO:5/SEQ ID NO:6): SEQ ID NO:5: 5'-CUUACGCUGAGUACUUCGA(dT)$_5$-3'; SEQ ID NO:6: 3'-(dA)$_5$GAAUGCGACUCAUGAAGCU-5'.

FIG. 3: RNA interference by (dA)$_5$-GL3Luc-(dT)$_5$ dsRNA (SEQ ID NOs: 5 and 6) duplexes mediates sequence-specific RNA interference.

A549-GL3Luc cells were transfected with (dA)$_5$-GL3Luc-(dT)$_5$ dsRNA (SEQ ID NOs: 5 and 6), a sequence mutated at position 9 (dA)$_5$-GL3Luc-(dT)$_5$ Mut dsRNA (SEQ ID NOs: 7 and 8), and (dA)$_5$-GL2Luc-(dT)$_5$ dsRNA (SEQ ID NOs: 9 and 10) duplexes complexed with jetPEI™. Luciferase gene expression was measured after 48 h incubation period. Experiments were made in triplicate and the luciferase silencing efficiency was calculated from the endogenous luciferase level of nontransfected A549-GL3Luc cells normalized by the content of protein in cell lysates.

(dA)$_5$-GL3Luc-(dT)$_5$ dsRNA (SEQ ID NO:5/SEQ ID NO:6): SEQ ID NO:5: 5'-CUUACGCUGAGUACUUCGA(dT)$_5$-3'; SEQ ID NO:6: 3'-(dA)$_5$GAAUGCGACUCAUGAAGCU-5'; (dA)$_5$-GL3Luc-(dT)$_5$ Mut dsRNA(SEQ ID NO:7/SEQ ID NO:8): SEQ ID NO:7: 5'-CUUACGCUAAGUACUUCGA(dT)$_5$-3'; SEQ ID NO:8: 3'-(dA)$_5$GAAUGCGAUUCAUGAAGCU-5'; (dA)$_5$-GL2Luc-(dT)$_5$ dsRNA(SEQ ID NO:9/SEQ ID NO:10): SEQ ID NO:9: 5'-CGUACGCGGAAUACUUCGA(dT)$_5$-3'; SEQ ID NO:10: 3'-(dA)$_5$GCAUGCGCCUUAUGAAGCU-5'.

FIG. 4: Double-stranded RNA having 3'-overhang that induce their intermolecular oligomerization when complexed with jetPEI™ mediates high GL3Luciferase silencing.

A549-GL3Luc cells were transfected with (dA)$_5$-GL3Luc-(dT)$_5$ dsRNA (SEQ ID NOs: 5 and 6), and (dA)$_8$-GL3Luc-(dT)$_8$ dsRNA (SEQ ID NOs: 12 and 13) duplexes complexed with jetPEI™. Luciferase gene expression was measured after 48 h incubation period. As dsRNAs that are unable to promote their intermolecular oligomerization by their 3' overhang, (dT)$_5$-GL3Luc-(dT)$_5$ dsRNA (SEQ ID NOs: 5 and 11) and (dT)$_8$-GL3Luc-(dT)$_8$ dsRNA (SEQ ID NOs: 12 and 14) duplexes were transfected in the same conditions with jetPEI™. Experiments were made in triplicate and the luciferase silencing efficiency was calculated from the endogenous luciferase level of nontransfected A549-GL3Luc cells normalized by the content of protein in cell lysates.

(dA)$_5$-GL3Luc-(dT)$_5$ dsRNA(SEQ ID NO:5/SEQ ID NO:6): SEQ ID NO:5: 5'-CUUACGCUGAGUACUUCGA(dT)$_5$-3'; SEQ ID NO:6: 3'-(dA)$_5$GAAUGCGACUCAUGAAGCU-5'; (dT)$_5$-GL3Luc-(dT)$_5$ dsRNA(SEQ ID NO:5/SEQ ID NO:11): SEQ ID NO:5: 5'-CUUACGCUGAGUACUUCGA(dT)$_5$-3'; SEQ ID NO:11: 3'-(dT)$_5$GAAUGCGACUCAUGAAGCU-5'; (dA)$_8$-GL3Luc-(dT)$_8$ dsRNA(SEQ ID NO:12/SEQ ID NO:13): SEQ ID NO:12: 5'-CUUACGCUGAGUACUUCGA(dT)$_8$-3'; SEQ ID NO:13: 3'-(dA)$_8$GAAUGCGACUCAUGAAGCU-5'; (dT)$_8$-GL3Luc-(dT)$_8$ dsRNA(SEQ ID NO:12/SEQ ID NO:14): SEQ ID NO:12: 5'-CUUACGCUGAGUACUUCGA(dT)$_8$-3'; SEQ ID NO:14: 3'-(dT)$_8$GAAUGCGACUCAUGAAGCU-5'.

FIG. 5: Double-stranded RNA having 3'-overhang that induce their intermolecular oligomerization when complexed with jetPEI™ mediates a sequence-specific GL3Luciferase silencing.

A549-GL3Luc cells were transfected with (dA)$_5$-GL3Luc-(dT)$_5$ dsRNA (SEQ N°3), and (dA)$_8$-GL3Luc-(dT)$_8$ dsRNA (SEQ ID NOs: 12 and 13) duplexes complexed with jetPEI™. Luciferase gene expression was measured after 48 h incubation period. As nonspecific control, (dA)$_5$-GL2Luc-(dT)$_5$ dsRNA (SEQ ID NOs: 9 and 10) and (dA)$_8$-GL2Luc-(dT)$_8$ dsRNA (SEQ ID NOs: 15 and 16) were transfected in the same conditions with jetPEI™. Experiments were made in triplicate and the luciferase silencing efficiency was calculated from the endogenous luciferase level of nontransfected A549-GL3Luc cells normalized by the content of protein in cell lysates.

(dA)$_5$-GL3Luc-(dT)$_5$ dsRNA(SEQ ID NO:5/SEQ ID NO:6): SEQ ID NO:5: 5'-CUUACGCUGAGUACUUCGA(dT)$_5$-3'; SEQ ID NO:6: 3'-(dA)$_5$GAAUGCGACUCAUGAAGCU-5'; (dA)$_5$-GL2Luc-(dT)$_5$ dsRNA(SEQ ID NO:9/SEQ ID NO:11): SEQ ID NO:9: 5'-CGUACGCGGAAUACUUCGA(dT)$_5$-3'; SEQ ID NO:11: 3'-(dA)$_5$GCAUGCGCCUUAUGAAGCU-5'; (dA)$_8$-GL3Luc-(dT)$_8$ dsRNA(SEQ ID NO:12/SEQ ID NO:13): SEQ ID NO:12: 5'-CUUACGCUGAGUACUUCGA(dT)$_8$-3'; SEQ ID NO:13: 3'-(dA)$_8$GAAUGCGACUCAUGAAGCU-5'; (dA)$_8$-GL2Luc-(dT)$_8$ dsRNA(SEQ ID NO:15/SEQ ID NO:16): SEQ ID NO:15: 5'-CGUACGCGGAAUACUUCGA(dT)$_8$-3'; SEQ ID NO:16: 3'-(dA)$_8$GCAUGCGCCUUAUGAAGCU-5'.

FIG. 6: Oligomerization of dsRNA promoted by intermolecular interactions using a linker interacting with symmetric 3' overhangs of dsRNAs duplexes mediates efficient GL3Luciferase silencing when complexed with jetPEI™

A549-GL3Luc cells were transfected with (dT)$_5$-GL3Luc-(dT)$_5$ dsRNA (SEQ ID NOs: 5 and 11), and (dT)$_8$-GL3Luc-(dT)$_8$ dsRNA (SEQ ID NOs: 12 and 14) duplexes without or with (dA)$_{15}$ (SEQ ID NOs: 17) and (dA)$_{25}$ (SEQ ID NO: 18) linkers, respectively, complexed with jetPEI™. Luciferase gene expression was measured after a 48 h incubation period. Experiments were made in triplicate and the luciferase silencing efficiency was calculated from the endogenous luciferase level of nontransfected A549-GL3Luc cells normalized by the content of protein in cell lysates.

$(dT)_5$-GL3Luc-$(dT)_5$ dsRNA(SEQ ID NO:5/SEQ ID NO:12): SEQ ID NO:5: 5'-CUUACGCUGAGUACUUCGA$(dT)_5$-3'; SEQ ID NO:12: 3'-$(dT)_5$GAAUGCGACUCAUGAAGCU-5'; $(dT)_8$-GL3Luc-$(dT)_8$ dsRNA(SEQ ID NO:12/SEQ ID NO:14): SEQ ID NO:12: 5'-CUUACGCUGAGUACUUCGA$(dT)_8$-3'; SEQ ID NO:14: 3'-$(dT)_8$GAAUGCGACUCAUGAAGCU-5'; $(dA)_{15}$ (SEQ ID NO:17): 5'-$(dA)_{15}$-3'; $(dA)_{25}$ (SEQ ID NO:18): 5'-$(dA)_{25}$-3'.

FIG. 7: Oligomerization of dsRNA promoted by intermolecular interactions using a linker interacting with symmetric 3' overhangs of dsRNAs duplexes mediates efficient GL3Luciferase silencing when complexed with a cationic lipid formulations such as jetSi-ENDO™ or RNAiFect.

A549-GL3Luc cells were transfected with $(dT)_2$-GL3Luc-$(dT)_2$ siRNA (SEQ ID NOs: 1 and 2), $(dT)_5$-GL3Luc-$(dT)_5$ dsRNA (SEQ ID NOs: 5 and 11), and $(dT)_8$-GL3Luc-$(dT)_8$ dsRNA (SEQ ID NOs: 12 and 14) duplexes with $(dA)_{15}$ (SEQ ID NO: 17) and $(dA)_{24}$ (SEQ ID NO: 18) linkers, for the sequences SEQ ID NOs: 5+11 and 12+13, respectively, complexed with jetSi-ENDO™ (a) and RNAiFect (b). Luciferase gene expression was measured after 48 h incubation period. Experiments were made in triplicate and the luciferase silencing efficiency was calculated from the endogenous luciferase level of nontransfected A549-GL3Luc cells normalized by the content of protein in cell lysates.

GL3Luc siRNA(SEQ ID NO:1/SEQ ID NO:2): SEQ ID NO:1: 5'-CUUACGCUGAGUACUUCGA$(dT)_2$-3'; SEQ ID NO:2: 3'-$(dT)_2$GAAUGCGACUCAUGAAGCU-5'; $(dT)_5$-GL3Luc-$(dT)_5$ dsRNA(SEQ ID NO:5/SEQ ID NO:11): SEQ ID NO:5: 5'-CUUACGCUGAGUACUUCGA$(dT)_5$-3'; SEQ ID NO:11: 3'-$(dT)_5$GAAUGCGACUCAUGAAGCU-5'; $(dT)_5$-GL3Luc-$(dT)_5$ dsRNA(SEQ ID NO:12/SEQ ID NO:14): SEQ ID NO:12: 5'-CUUACGCUGAGUACUUCGA$(dT)_8$-3'; SEQ ID NO:14: 3'-$(dT)_8$GAAUGCGACUCAUGAAGCU-5'; $(dA)_{15}$ (SEQ ID NO:17): 5'-$(dA)_{15}$-3'; $(dA)_{25}$ (SEQ ID NO:18): 5'-$(dA)_{25}$-3'.

MATERIALS AND METHODS

Chemicals and Oligonucleotides

Oligonucleotides were chemically synthesised and PAGE purified by Eurogentec (Belgium). Oligonucleotides were annealed in 1× Annealing buffer (50 mM KAcetate, 50 mM MgAcetate) (Eurogentec) for 2 min. at 95° C., followed by 2-4 hours incubation at room temperature.

jetSi-ENDO™ (cationic lipid reagent for siRNA transfection) and jetPEI™ (cationic polymer, linear polyethylenimine derivative, for nucleic acid transfection) were from Polyplus-Transfection (France). RNAifect was from Qiagen (United State).

Cell Culture

A549 (human lung carcinoma, ATCC N° CCL-185) cells stably expressing the GL3 luciferase (Photinus pyralis luciferase under the control of SV40 elements) were obtained after stable transfection of pGL3Luc plasmid (Clontech). A549-GL3Luc cells were grown in RPMI (Eurobio, France) and supplemented with 10% fetal bovine serum (FBS, Perbio, France), 2 mM glutamax (Eurobio), 100 units/ml penicillin (Eurobio), 100 µg/ml streptomycin (Eurobio) and 0.8 µg/ml G418 (Promega). Cells were maintained at 37° C. in a 5% $CO_2$ humidified atmosphere.

Transfection Experiments

One day before transfection, $2.5 \times 10^4$ cells were seeded in 24-well tissue culture plate in 1 ml fresh complete medium containing 10% FBS. Before transfection, complexes of dsRNA/transfection reagent were prepared. The desired amount of oligonucleotides, dsRNAs with or without oligonucleotide linkers, and transfection reagent were diluted in 150 µl of serum-free medium for jetSi-ENDO™ or 150 µl of NaCl 150 mM for jetPEI™ (for a triplicate experiment). Three and 2 µl of jetSi-ENDO™ and jetPEI™ were used per µg of dsON, respectively. The solutions were mixed with a Vortex for 10 seconds, and left for 10 minutes at room temperature. The transfection reagent was added to the dsRNAs solution, homogenized for 10 seconds with a Vortex and left 30 minutes at room temperature. Before adding the transfection complexes, the complete medium with serum was removed and replaced with 0.5 ml of serum-free medium. Then, 100 µl of complexes solution was added per well and the plates were incubated at 37° C. After 2 h of incubation, the complete medium was removed and replace with 1 ml of complete medium containing 10% serum. For RNAifect, the desired amount of dsRNAs and oligonucleotide linkers was diluted in 300 µl of serum free medium (for triplicate experiment). Then, the transfection reagent was added to the siRNA mixture (3 µl of RNAifect per µg of dsON). The solution was mixed with a vortex, 10 seconds and left for 15 minutes at room temperature. Before adding the transfection complexes, the complete medium with serum was removed and replaced with 0.3 ml of complete medium with serum. 100 µl of complexes solution were added per well and the plates are incubated at 37° C. After 24 h, the culture medium was removed and replaced by 0.5 ml of complete medium containing 10% serum. For all transfection protocol, the plate was further incubated at 37° C. for 24 or 48 h.

Luciferase and Protein Assay

Luciferase gene expression was measured using a commercial kit (Promega, France). After removing the complete medium, three washings with 1 ml of PBS solution were made. Then, 100 µl of 1× lysis buffer were added per well, and the plate was incubated at room temperature for 30 minutes. The lysates were collected and centrifuged at 14,000 g for 5 minutes. The luciferase assay was assessed with 5 µl of lysate after injection of 100 µl of luciferin solution. The luminescence (RLU) was monitored with an integration over 10 seconds with a luminometer (Berthold, France). Results are expressed as light units integrated over 10 seconds (RLU), per mg of cell protein using the BCA assay (Pierce, France).

Results

As a target model of endogenous gene, we used the A549 cells stably expressing the GL3 luciferase (Photinus pyralis luciferase under the control of SV40 elements). A well-defined chemically produced siRNA, directed against GL3 luciferase mRNA was transfected with a typical cationic lipid-based delivery reagent (jetSi-ENDO™) and a typical cationic polymer-based delivery reagent (jetPEI™) in the nanomolar concentration range of siRNA. The sequence-specific classical GL3Luc siRNA was a short dsRNA of 19 nucleotides matching the GL3Luc mRNA and comprising identical (i.e. noncomplementary) 3'-overhangs of 2 deoxyribonucleotides (dT) according to the definition of preferable siRNA mediating RNAi in mammalian cells (Elbashir et al., 2001). The silencing efficiency of GL3 luciferase presented in the FIG. 1 reached 70% and more than 80%, 24 and 48 h after transfection, respectively, when the transfection was performed with jetSi-ENDO™ and at 75 nM of siRNA. The low silencing level of GL2Luc siRNA, used as unrelated sequence, confirmed a sequence-specific RNAi. The sequence-specific silencing of GL3 luciferase was also observed when the transfection was performed with jetPEI™, yet, with a lower efficiency and duration than transfection with the cationic lipid derivative.

In order to improve the silencing efficiency of dsRNA mediating RNAi, we used a dsRNA (SEQ ID NOs: 5 and 6) of 19 nucleotides matching the GL3 Luc mRNA and comprising 3'-overhangs with 5 deoxythymidine nucleotides at the end of the antisens strand and 5 deoxyguanosine nucleotides at the end of sense strand. These 3' overhangs can promote a 3' overhang-3' overhang interaction leading to intermolecular oligomerization of dsRNA into longer dsRNA. After transfection of A549-GL3Luc cells with (dA)$_5$-GL3Luc-(dT)$_5$ dsRNA (SEQ 5 and 6) complexed with jetPEI™ (FIG. 2), a high luciferase silencing is observed (>80% at 50-75 nM of dsRNA, 24 and 48 h post-transfection). (dA)$_5$-GL3Luc-(dT)$_5$ dsRNA (SEQ ID NOs: 5 and 6) mediated a better luciferase gene silencing than standard siRNA transfected with both jetSi-ENDO™ and jetPEI™ reagents. Gene silencing with (dA)$_5$-GL3Luc-(dT)$_5$ dsRNA (SEQ ID NOs: 5 and 6) was particularly efficient at 10 nM concentration 48 h post-transfection where GL3Luc siRNA was unable to silence luciferase expression when introduced by either delivery reagents used (FIG. 2).

A single nucleotide substitution in the sequence-specific (dA)$_5$-GL3Luc-(dT)$_5$ dsRNA (SEQ 5 and 6) was introduced at the position 9 (A versus G in the antisens strand) to abolish the specific recognition of GL3Luc mRNA target. This single-mutated sequence, (dA)$_5$-GL3Luc-(dT)$_5$-Mut dsRNA (SEQ ID NOs: 7 and 8), was introduced into A549-GL3Luc cells with jetPEI™. It was unable to silence luciferase expression (FIG. 3) 48 h post-transfection in the concentration range of 5 to 50 nM. As other control of selectivity, (dA)$_5$-GL2Luc-(dT)$_5$ dsRNA (SEQ ID NOs: 9 and 10), matching the unrelated GL2 luciferase, was transfected and was also unable to silence luciferase expression (FIG. 3).

The length of 3' overhangs of oligomerizable dsRNAs was studied using 5 or 8 nucleotides at the 3'-protusions of the duplexes. Both (dA)$_5$-GL3Luc-(dT)$_5$ dsRNA (SEQ ID NOs: 5 and 6) and (dA)$_8$-GL3Luc-(dT)$_8$ dsRNA (SEQ ID NOs: 12 and 13) showed efficient and comparable level of silencing 48 h post-transfection when introduced with jetPEI in A549-GL3Luc cells (FIG. 4). As controls, (dT)$_5$-GL3Luc-(dT)$_5$ dsRNA (SEQ ID NOs: 5 and 11) and (dT)$_8$-GL3Luc-(dT)$_8$ dsRNA (SEQ ID NOs: 12 and 14), which are unable to promote their oligomerization, were much less efficient to silence luciferase expression compared the results obtained with oligomerisable dsRNAs, SEQ ID NOs: 5 and 6 and 7 (FIG. 4). A control of silencing selectivity was performed with oligomerizable dsRNAs having 5 or 8 nucleotides at the 3'-end of each strand of duplexes but matching the GL2 sequence. Both (dA)$_5$-GL2Luc-(dT)$_5$ dsRNA (SEQ ID NOs: 9 and 10) and (dA)$_8$-GL3Luc-(dT)$_8$ dsRNA (SEQ ID NOs: 15 and 16) were inefficient to silence the endogenously-expressed GL3 luciferase (FIG. 5).

Oligomerization of short dsONs mediating RNAi can be promoted by an oligonucleotide linker which recognizes by base pairing the 3'-overhangs of dsON duplexes by base pairing. As a model, (dT)$_5$-GL3Luc-(dT)$_5$ dsRNA (SEQ ID NOs: 5 and 11) and (dT)$_8$-GL3Luc-(dT)$_8$ dsRNA (SEQ ID NOs: 12 and 14) were introduced into A549-Gl3Luc cells with jetPEI™ in the presence or absence of poly(dA) nucleotides. Poly(dA) comprising 15 (SEQ ID NO: 17) and 25 (SEQ ID NO: 18) nucleotides in length were used to promote the oligomerization of duplexes of SEQ ID NOs: 5+12 and 12+14, respectively. When the poly(dA) linkers were present, luciferase silencing was highly efficient for both dsRNA duplexes as compared to the silencing efficiencies obtained in the absence of poly(dA) linkers (FIG. 6). The dsRNA with 3' overhangs with a length of 5 nucleotides showed the best silencing ability in the presence of (dA)$_{15}$ linker in this example (FIG. 6). Oligomerization of dsRNA mediating RNAi with an oligonucleotide linker thus increased its efficacy.

Composition comprising dsONs oligomerized by an oligonucleotide linker which recognizes by base pairing the 3'-overhangs of dsON duplexes and delivered into cells with a cationic lipid based transfection reagent, such as jetSi-ENDO™ or RNAiFect delivery reagents, mediates specific GL3 luciferase gene silencing in A549-GL3Luc cells. Poly (dA) was used as linker comprising 15 (SEQ ID NO: 17) and 25 (SEQ ID NO: 18) nucleotides in length to promote the oligomerization of duplexes of SEQ ID NOs: 5 and 6, respectively. When the poly(dA) linkers were present, luciferase silencing was highly efficient at the nanomolar level for both dsRNA duplexes as compared to the silencing efficiencies obtained with the typical GL3Luc siRNA (SEQ N° 1) (FIG. 7). Oligomerization of dsRNA mediating RNAi with an oligonucleotide linker increased the gene silencing efficiency as compared to the conventional strategy using siRNA when introduced into cells with a cationic lipid-based delivery system.

| Sequences | |
|---|---|
| SEQ ID NOs: 1 and 2: GL3Luc siRNA | 5'-CUUACGCUGAGUACUUCGA(dT)$_2$-3'<br>3'-(dT)$_2$GAAUGCGACUCAUGAAGCU-5' |
| SEQ ID NOs: 3 and 4: GL2Luc siRNA | 5'-CGUACGCGGAAUACUUCGA(dT)$_2$-3'<br>3'-(dT)$_2$GCAUGCGCCUUAUGAAGCU-5' |
| SEQ ID NOs: 5 and 6: (dA)$_5$-GL3Luc-(dT)$_5$ dsRNA | 5'-CUUACGCUGAGUACUUCGA(dT)$_5$-3'<br>3'-(dA)$_5$GAAUGCGACUCAUGAAGCU-5' |
| SEQ ID NOs: 7 and 8: (dA)$_5$-GL3Luc-(dT)$_5$ Mut dsRNA | 5'-CUUACGCUAAGUACUUCGA(dT)$_5$-3'<br>3'-(dA)$_5$GAAUGCGAUUCAUGAAGCU-5' |
| SEQ ID NOs: 9 and 10: (dA)$_5$-GL2Luc-(dT)$_5$ dsRNA | 5'-CGUACGCGGAAUACUUCGA(dT)$_5$-3'<br>3'-(dA)$_5$GCAUGCGCCUUAUGAAGCU-5' |
| SEQ ID NOs: 5 + 11: (dT)$_5$-GL3Luc-(dT)$_5$ dsRNA | 5'-CUUACGCUGAGUACUUCGA(dT)$_5$-3'<br>3'-(dT)$_5$GAAUGCGACUCAUGAAGCU-5' |
| SEQ ID NOs: 12 + 13: (dA)$_8$-GL3Luc-(dT)$_8$ dsRNA | 5'-CUUACGCUGAGUACUUCGA(dT)$_8$-3'<br>3'-(dA)$_8$GAAUGCGACUCAUGAAGCU-5' |
| SEQ ID NOs: 12 + 14: (dT)$_8$-GL3Luc-(dT)$_8$ dsRNA | 5'-CUUACGCUGAGUACUUCGA(dT)$_8$-3'<br>3'-(dT)$_8$GAAUGCGACUCAUGAAGCU-5' |
| SEQ ID NOs: 15 + 16: (dA)$_8$-GL2Luc-(dT)$_8$ dsRNA | 5'-CGUACGCGGAAUACUUCGA(dT)$_8$-3'<br>3'-(dA)$_8$GCAUGCGCCUUAUGAAGCU-5' |
| SEQ ID NO: 17: (dA)$_{15}$ | 5'-(dA)$_{15}$-3' |
| SEQ ID NO: 18: (dA)$_{25}$ | 5'-(dA)$_{25}$-3' |

BIBLIOGRAPHIC REFERENCES

Elbashir, S M et al. (2001) Duplexes of 21-nucleotide RNAs mediate RNA interference in mammalian cell culture. Nature 411: 494-498.

Elbashir, S M et al. (2001) RNA interference is mediated by 21 and 22 nt RNAs. Genes & Dev. 15: 188-200.

Fire, A. (1999) RNA-triggered gene silencing. *Trends Genet.* 15, 358-363. Ge, Q et al. (2004) Inhibition of influenza virus production in virus infected mice by RNA interference. PNAS 101, 8676-8681.
Guan, H. (2005) A small interfering RNA targeting vascular endothelial growth factor inhibits Ewing's sarcoma growth in a xenograft mouse model, *Clin Cancer Res* 7, 2662-2669.
Hammond, S M et al. (2000) An RNA-directed nuclease mediates post-transcriptional gene silencing in *Drosophila* cells. *Nature* 404, 363-366.
Jepsen J S, Wengel J. (2004) LNA-antisense rivals siRNA for gene silencing. *Curr Opin Drug Discov Devel.* 7(2):188-94.
Kim, D H et al. (2005) Synthetic dsRNA Dicer substrates enhance RNAi potency and efficacy. Nature Biotech. 23, 222-226.
Kurreck J. (2003) Antisense technologies. Improvement through novel chemical modifications. *Eur J Biochem.* 270 (8):1628-44.
Miller P S. (1991) Oligonucleoside methylphosphonates as antisense reagents. *Biotechnology* (N Y) 9(4):358-62.
Pal, A. et al. (2005) Systemic delivery if RafsiRNA using cationic cardiolipin liposomes silences Raf-1 expression and inhibits tumor growth in xenograft model of human prostate cancer, *Int J Oncol,* 26, 1087-91
Parrish, S. et al. (2000) Functional anatomy of a dsRNA trigger: differential requirement for the two trigger strand in RNA interference. *Mol Cell.* 6, 1077-1087.
Siolas, D et al. (2005) Synthetic shRNAs as potent RNAi triggers. *Nature biotech.* 23, 227-231.
Tuschl, T. (2001) RNA interference and small interfering RNAs. *Chembiochem.* 2, 239-245.
Tuschl, T. et al. (1999) Targeted mRNA degradation by double-stranded RNA in vitro. Genes & Dev. 13, 3191-3197.
Urban-Klein, B. et al. (2004) RNAi-mediated gene-targeting through systemic application of polyethylenimine (PEI)-complexed siRNA in vivo, *Gene Therapy* 23, 1-6
Verma S, Eckstein F. (1998) Modified oligonucleotides: synthesis and strategy for users. *Annu Rev Biochem.* 67:99-134.
Vester B, Wengel J. (2004) LNA (locked nucleic acid): high-affinity targeting of complementary RNA and DNA. *Biochemistry.* 43(42):13233-41.
Yang, D, et al. (2000) Evidence that processed small dsRNAs may mediate sequence-specific mRNA degradation during RNAi in *Drosophila* embryos. *Curr Biol.* 10, 1191-1200.
Zamore, P D et al. (2000) RNAi: Double-stranded RNA directs the ATP-dependent cleavage of mRNA at 21 to 23 nucleotides intervals. Cell 101, 25-33.
Zon G, Geiser T G. (1991) Phosphorothioate oligonucleotides: chemistry, purification, analysis, scale-up and future directions. *Anticancer Drug Des.* 6(6):539-68.

We claim:

1. A composition for RNA interference comprising oligomerized double-stranded nucleic acids, said oligomerized double-stranded nucleic acids comprising a plurality of identical or different double-stranded nucleic acids and, optionally, a linker,
    wherein each of said identical or different double-stranded nucleic acids consists of a first distinct oligonucleotide and a second distinct oligonucleotide,
    wherein each of said first and second distinct oligonucleotides consists of 19-28 ribonucleotides at the 5'-end and 3-50 dT or dT and dA nucleotides at the 3'-end,
    wherein the 19-28 ribonucleotides at the 5'-end of the first distinct oligonucleotide are base-paired to the 19-28 ribonucleotides at the 5'-end of the second distinct oligonucleotide and wherein the 3-50 dT or dT and dA nucleotides at the 3'-end of the first distinct oligonucleotide and at the 3'-end of the second distinct oligonucleotide are unpaired overhanging sticky dT or dT and dA nucleotides,
    such that the unpaired overhanging sticky dT or dT and dA nucleotides at the 3'-end of the first distinct oligonucleotide of one of the plurality of identical or different double-stranded nucleic acids are complementary to the unpaired overhanging sticky dT or dT and dA nucleotides at the 3'-end of the second distinct oligonucleotide of another of the plurality of identical or different double-stranded nucleic acids or to a linker having unpaired overhanging sticky dT or dT and dA nucleotides, and wherein said complementary unpaired overhanging sticky dT or dT and dA nucleotides of the plurality of identical or different double-stranded nucleic acids or of the linker are hybridized to form said oligomerized double-stranded nucleic acids.

2. The composition of claim 1, wherein each of said first and second distinct oligonucleotides consists of 19-21 ribonucleotides at the 5'-end and 3-50 dT or dT and dA nucleotides at the 3' end,
    said 19-21 ribonucleotides of said each first distinct oligonucleotide or said 19-21 ribonucleotides of said each second distinct oligonucleotide being complementary to at least one target nucleic acid sequence in a living cell.

3. The composition of claim 1, wherein the unpaired overhanging sticky dT or dT and dA nucleotides of said each first distinct oligonucleotide and said each second distinct oligonucleotide consists of 5-8 nucleotides.

4. The composition of claim 1, wherein at least one of said 19-28 ribonucleotides of said each first or second distinct oligonucleotide is a modified ribonucleotide.

5. The composition of claim 4, wherein the modified ribonucleotide is selected from the group consisting of a nucleotide analogue, a sugar-modified ribonucleotide, and a sugar-backbone modified ribonucleotide.

6. The composition of claim 1, wherein the linker is selected from the group consisting of oligonucleotides, single-stranded oligonucleotides, hairpin structures, short double stranded nucleic acids having 3' or 5' overhangs and double stranded oligonucleotides.

7. A composition for RNA interference comprising oligomerized double-stranded nucleic acids, said oligomerized double stranded nucleic acids comprising a plurality of identical or different double-stranded nucleic acids and, optionally a linker,
    wherein each of said identical or different double-stranded nucleic acids consists of a first distinct oligonucleotide and a second distinct oligonucleotide,
    wherein each of said first and second distinct oligonucleotides consists of 19-28 ribonucleotides at the 5'-end and 3-50 dT or dT and dA nucleotides at the 3'-end,
    wherein the 19-28 ribonucleotides at the 5'-end of the first distinct oligonucleotide are base-paired to the 19-28 ribonucleotides at the 5'-end of the second distinct oligonucleotide and wherein the 3-50 dT or dT and dA nucleotides at the 3'-end of the first distinct oligonucleotide and at the 3'-end of the second distinct oligonucleotide are unpaired overhanging sticky dT or dT and dA nucleotides,
    such that the unpaired overhanging sticky dT or dT and dA nucleotides at the 3'-end of the first distinct oligonucleotide of one of the plurality of identical or different double-stranded nucleic acids are complementary to the unpaired overhanging sticky dT or dT and dA nucleotides at the 3'-end of the second distinct oligonucleotide of another of the plurality of identical or different double-stranded nucleic acids or to a linker having unpaired overhanging sticky dT or dT and dA nucleotides, and wherein said complementary unpaired overhanging sticky dT or dT and dA nucleotides of the plurality of identical or different double-stranded nucleic acids or of the linker are hybridized to form said oligomerized double-stranded nucleic acids; and
    a transfection agent or transfection formulation that liberates said oligomerized double-stranded nucleic acids in cytoplasm upon transfection.

8. The composition of claim 7, wherein said transfection agent is selected from the group consisting of a cationic lipid and a cationic polymer.

9. The composition of claim 8, wherein the cationic polymer is a polyethylenimine derivative.

10. The composition of claim 7, wherein the linker is selected from the group consisting of oligonucleotides, single-stranded oligonucleotides, hairpin structures, short double stranded nucleic acids having 3' or 5' overhangs and double stranded oligonucleotides.

11. A composition for RNA interference comprising oligomerized double-stranded nucleic acids, said oligomerized double stranded nucleic acids comprising a plurality of identical or different double-stranded nucleic acids and, optionally a linker,
    wherein each of said identical or different double-stranded nucleic acids consists of a first distinct oligonucleotide and a second distinct oligonucleotide,
    wherein each of said first and second distinct oligonucleotides consists of 19-28 ribonucleotides at the 5'-end and 3-50 dT or dT and dA nucleotides at the 3'-end,
    wherein the 19-28 ribonucleotides at the 5'-end of the first distinct oligonucleotide are base-paired to the 19-28 ribonucleotides at the 5'-end of the second distinct oligonucleotide and wherein the 3-50 dT or dT and dA nucleotides at the 3'-end of the first distinct oligonucleotide and at the 3'-end of the second distinct oligonucleotide are unpaired overhanging sticky dT or dT and dA nucleotides,
    such that the unpaired overhanging sticky dT or dT and dA nucleotides at the 3'-end of the first distinct oligonucleotide of one of the plurality of identical or different double-stranded nucleic acids are complementary to the unpaired overhanging sticky dT or dT and dA nucleotides at the 3'-end of the second distinct oligonucleotide of another of the plurality of identical or different double-stranded nucleic acids or to a linker having unpaired overhanging sticky dT or dT and dA nucleotides, wherein said complementary unpaired overhanging sticky dT or dT and dA nucleotides of the plurality of identical or different double-stranded nucleic acids or of the linker are hybridized to form said oligomerized double-stranded nucleic acids, and wherein the linker is selected from the group consisting of oligonucleotides, single-stranded oligonucleotides, hairpin structures, short double stranded nucleic acids having 3' or 5' overhangs and double stranded oligonucleotides; and
a polyethylenimine derivative.

* * * * *

SEQUENCE LISTING

```
<160> NUMBER OF SEQ ID NOS: 18

<210> SEQ ID NO 1
<211> LENGTH: 21
<212> TYPE: DNA
<213> ORGANISM: Artificial sequence
<220> FEATURE:
<223> OTHER INFORMATION: Oligonucleotide
<220> FEATURE:
<221> NAME/KEY: modified_base
<222> LOCATION: (20)..(21)
<223> OTHER INFORMATION: Desoxythymidine

<400> SEQUENCE: 1
cuuacgcuga guacuucgat t                                              21

<210> SEQ ID NO 2
<211> LENGTH: 21
<212> TYPE: DNA
<213> ORGANISM: Artificial sequence
<220> FEATURE:
<223> OTHER INFORMATION: Oligonucleotide
<220> FEATURE:
<221> NAME/KEY: modified_base
<222> LOCATION: (20)..(21)
<223> OTHER INFORMATION: 5'-3' Desoxythymidine

<400> SEQUENCE: 2
ucgaaguacu cagcguaagt t                                              21

<210> SEQ ID NO 3
<211> LENGTH: 21
<212> TYPE: DNA
<213> ORGANISM: Artificial sequence
<220> FEATURE:
<223> OTHER INFORMATION: Oligonucleotide
<220> FEATURE:
<221> NAME/KEY: modified_base
<222> LOCATION: (20)..(21)
<223> OTHER INFORMATION: Desoxythymidine
```

<400> SEQUENCE: 3
cguacgcgga auacuucgat t                                              21

<210> SEQ ID NO 4
<211> LENGTH: 21
<212> TYPE: DNA
<213> ORGANISM: Artificial sequence
<220> FEATURE:
<223> OTHER INFORMATION: Oligonucleotide
<220> FEATURE:
<221> NAME/KEY: modified_base
<222> LOCATION: (20)..(21)
<223> OTHER INFORMATION: 5'-3' Desoxythymidine

<400> SEQUENCE: 4
ucgaaguauu ccgcguacgt t                                              21

<210> SEQ ID NO 5
<211> LENGTH: 24
<212> TYPE: DNA
<213> ORGANISM: Artificial sequence
<220> FEATURE:
<223> OTHER INFORMATION: Oligonucleotide
<220> FEATURE:
<221> NAME/KEY: modified_base
<222> LOCATION: (20)..(24)
<223> OTHER INFORMATION: Desoxythymidine

<400> SEQUENCE: 5
cuuacgcuga guacuucgat tttt                                           24

<210> SEQ ID NO 6
<211> LENGTH: 24
<212> TYPE: DNA
<213> ORGANISM: Artificial sequence
<220> FEATURE:
<223> OTHER INFORMATION: Oligonucleotide
<220> FEATURE:
<221> NAME/KEY: modified_base
<222> LOCATION: (20)..(24)
<223> OTHER INFORMATION: 5'-3' Desoxyadenosine

<400> SEQUENCE: 6
ucgaaguacu cagcguaaga aaaa                                           24

<210> SEQ ID NO 7
<211> LENGTH: 24
<212> TYPE: DNA
<213> ORGANISM: Artificial sequence
<220> FEATURE:
<223> OTHER INFORMATION: Oligonucleotide
<220> FEATURE:
<221> NAME/KEY: modified_base
<222> LOCATION: (20)..(24)
<223> OTHER INFORMATION: Desoxythymidine

<400> SEQUENCE: 7
cuuacgcuaa guacuucgat tttt                                           24

<210> SEQ ID NO 8
<211> LENGTH: 24
<212> TYPE: DNA
<213> ORGANISM: Artificial sequence
<220> FEATURE:
<223> OTHER INFORMATION: Oligonucleotide
<220> FEATURE:
<221> NAME/KEY: modified_base
<222> LOCATION: (20)..(24)

```
<223> OTHER INFORMATION: 5'-3' Desoxyadenosine

<400> SEQUENCE: 8
ucgaaguacu uagcguaaga aaaa                                          24

<210> SEQ ID NO 9
<211> LENGTH: 24
<212> TYPE: DNA
<213> ORGANISM: Artificial sequence
<220> FEATURE:
<223> OTHER INFORMATION: Oligonucleotide
<220> FEATURE:
<221> NAME/KEY: modified_base
<222> LOCATION: (20)..(24)
<223> OTHER INFORMATION: Desoxythymidine

<400> SEQUENCE: 9
cguacgcgga auacuucgat tttt                                          24

<210> SEQ ID NO 10
<211> LENGTH: 24
<212> TYPE: DNA
<213> ORGANISM: Artificial sequence
<220> FEATURE:
<223> OTHER INFORMATION: Oligonucleotide
<220> FEATURE:
<221> NAME/KEY: modified_base
<222> LOCATION: (20)..(24)
<223> OTHER INFORMATION: 5'-3' Desoxyadenosine

<400> SEQUENCE: 10
ucgaaguauu ccgcguacga aaaa                                          24

<210> SEQ ID NO 11
<211> LENGTH: 24
<212> TYPE: DNA
<213> ORGANISM: Artificial sequence
<220> FEATURE:
<223> OTHER INFORMATION: Oligonucleotide
<220> FEATURE:
<221> NAME/KEY: modified_base
<222> LOCATION: (20)..(24)
<223> OTHER INFORMATION: 5'-3' Desoxythymidine

<400> SEQUENCE: 11
ucgaaguacu cagcguaagt tttt                                          24

<210> SEQ ID NO 12
<211> LENGTH: 27
<212> TYPE: DNA
<213> ORGANISM: Artificial sequence
<220> FEATURE:
<223> OTHER INFORMATION: Oligonucleotide
<220> FEATURE:
<221> NAME/KEY: modified_base
<222> LOCATION: (20)..(27)
<223> OTHER INFORMATION: Desoxythymidine

<400> SEQUENCE: 12
cuuacgcuga guacuucgat tttttt                                        27

<210> SEQ ID NO 13
<211> LENGTH: 27
<212> TYPE: DNA
<213> ORGANISM: Artificial sequence
<220> FEATURE:
<223> OTHER INFORMATION: Oligonucleotide
<220> FEATURE:
<221> NAME/KEY: modified_base
```

```
<222> LOCATION: (20)..(27)
<223> OTHER INFORMATION: 5'-3' desoxyadenosine

<400> SEQUENCE: 13
ucgaaguacu cagcguaaga aaaaaaa                                              27

<210> SEQ ID NO 14
<211> LENGTH: 27
<212> TYPE: DNA
<213> ORGANISM: Artificial sequence
<220> FEATURE:
<223> OTHER INFORMATION: Oligonucleotide
<220> FEATURE:
<221> NAME/KEY: modified_base
<222> LOCATION: (20)..(27)
<223> OTHER INFORMATION: 5'-3' desoxythymidine

<400> SEQUENCE: 14
ucgaaguacu cagcguaagt ttttttt                                              27

<210> SEQ ID NO 15
<211> LENGTH: 27
<212> TYPE: DNA
<213> ORGANISM: Artificial sequence
<220> FEATURE:
<223> OTHER INFORMATION: Oligonucleotide
<220> FEATURE:
<221> NAME/KEY: modified_base
<222> LOCATION: (20)..(27)
<223> OTHER INFORMATION: Desoxythymidine

<400> SEQUENCE: 15
cguacgcgga auacuucgat ttttttt                                              27

<210> SEQ ID NO 16
<211> LENGTH: 27
<212> TYPE: DNA
<213> ORGANISM: Artificial sequence
<220> FEATURE:
<223> OTHER INFORMATION: Oligonucleotide
<220> FEATURE:
<221> NAME/KEY: modified_base
<222> LOCATION: (20)..(27)
<223> OTHER INFORMATION: 5'-3' Desoxyadenosine

<400> SEQUENCE: 16
ucgaaguauu ccgcguacga aaaaaaa                                              27

<210> SEQ ID NO 17
<211> LENGTH: 15
<212> TYPE: DNA
<213> ORGANISM: Artificial sequence
<220> FEATURE:
<223> OTHER INFORMATION: Oligonucleotide

<400> SEQUENCE: 17
aaaaaaaaaa aaaaa                                                           15

<210> SEQ ID NO 18
<211> LENGTH: 25
<212> TYPE: DNA
<213> ORGANISM: Artificial sequence
<220> FEATURE:
<223> OTHER INFORMATION: Oligonucleotide

<400> SEQUENCE: 18
aaaaaaaaaa aaaaaaaaaa aaaaa                                                25
```